United States Patent
Lim et al.

(10) Patent No.: US 9,859,065 B1
(45) Date of Patent: Jan. 2, 2018

(54) HIGH VOLTAGE CAPACITOR WITH INCREASED ANODE SURFACE AREA AND METHOD OF MAKING SAME

(71) Applicant: PACESETTER, INC., Sylmar, CA (US)

(72) Inventors: Wisit Lim, Santa Clarita, CA (US); Ralph Jason Hemphill, Sunset, SC (US); Troy L. McCurry, West Union, SC (US); Peter Fernstrom, Easley, SC (US)

(73) Assignee: PACESETTER, INC., Sylmar, CA (US)

( * ) Notice: Subject to any disclaimer, the term of this patent is extended or adjusted under 35 U.S.C. 154(b) by 0 days.

(21) Appl. No.: 15/251,788

(22) Filed: Aug. 30, 2016

(51) Int. Cl.

| | |
|---|---|
| *H01G 11/54* | (2013.01) |
| *H01G 9/26* | (2006.01) |
| *H05K 1/18* | (2006.01) |
| *H01G 9/08* | (2006.01) |
| *H01G 9/145* | (2006.01) |
| *H01G 9/02* | (2006.01) |
| *H01G 9/048* | (2006.01) |
| *H01G 9/07* | (2006.01) |
| *A61N 1/39* | (2006.01) |

(52) U.S. Cl.
CPC ........... *H01G 11/54* (2013.01); *A61N 1/3956* (2013.01); *H01G 9/02* (2013.01); *H01G 9/048* (2013.01); *H01G 9/07* (2013.01); *H01G 9/08* (2013.01); *H01G 9/145* (2013.01); *H01G 9/26* (2013.01); *H05K 1/181* (2013.01); *H05K 2201/10015* (2013.01)

(58) Field of Classification Search
CPC ........ H01G 11/54; H01G 11/56; H01G 11/58; H01G 11/60; H01G 11/62; H01G 11/64; H01G 11/72; H01G 11/84; H01G 11/86
See application file for complete search history.

(56) References Cited

U.S. PATENT DOCUMENTS

| | | | | |
|---|---|---|---|---|
| 2005/0128678 A1* | 6/2005 | Hidaka | .................... | H01G 4/38 361/305 |
| 2014/0318843 A1* | 10/2014 | Han | ........................ | H01G 4/30 174/260 |

* cited by examiner

*Primary Examiner* — Jeremy C Norris

(57) ABSTRACT

An electrolytic capacitor is disclosed having a housing in an arced-trapezoidal shape. Disposed within the housing are one or more anodes, one or more cathodes, one or more separators disposed between anodes that are adjacent anodes cathodes, and an electrolyte disposed around the one or more anodes, the one or more cathodes, and the one or more separators within the housing. The housing of the electrolytic capacitor includes front and back walls shaped as arced-trapezoids and four sidewalls that substantially follow the outline of the front and back walls. The electrolytic capacitor is configured to connect in series with one or more electrolytic capacitors of the same shape to form a capacitor assembly. In the capacitor assembly, electrolytic capacitors are placed such that sidewalls are adjacent to each other to form a D-shaped capacitor assembly.

20 Claims, 8 Drawing Sheets

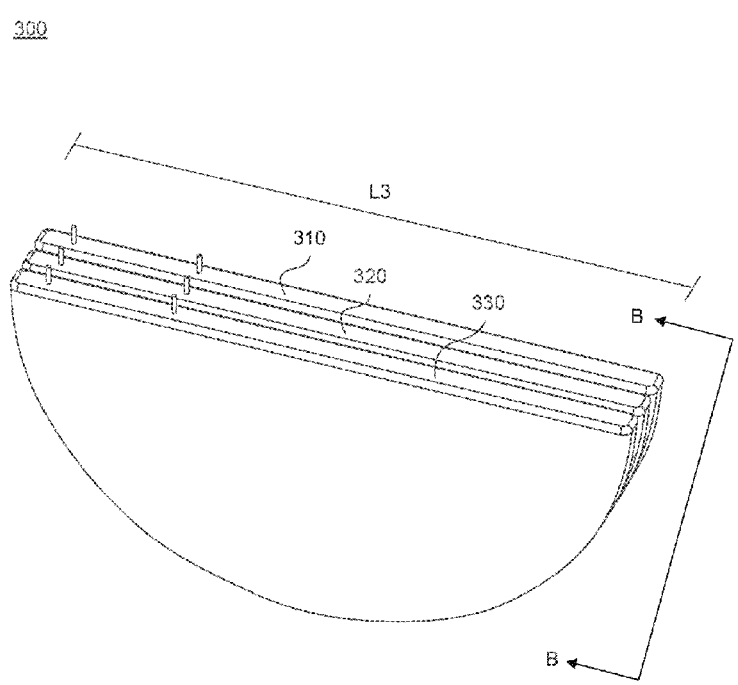
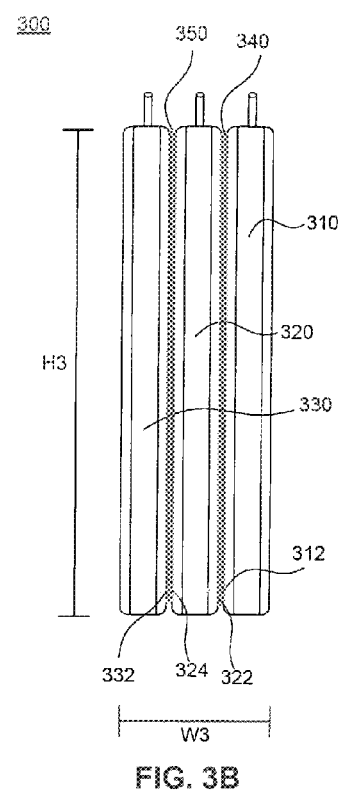
FIG. 3A
FIG. 3B

HIGH VOLTAGE CAPACITOR WITH INCREASED ANODE SURFACE AREA AND METHOD OF MAKING SAME

FIELD

The present invention relates generally to the field of electrolytic capacitors and, more specifically, to a high voltage capacitor with increased anode surface area and method of manufacturing the same.

BACKGROUND

Compact, high voltage capacitors are utilized as energy storage reservoirs in many applications, including implantable medical devices (IMDs). These capacitors are required to have a high energy density, since it is desirable to minimize the overall size of the implanted device. This is particularly true of an Implantable Cardioverter Defibrillator (ICD), also referred to as an implantable defibrillator, since the high voltage capacitors used to deliver the defibrillation pulse can occupy as much as one third of the ICD volume.

ICDs, such as those disclosed in U.S. Pat. No. 5,131,388, typically use two electrolytic capacitors in series to achieve the desired high voltage for shock delivery. For example, an ICD may utilize two 350 to 475 volt electrolytic capacitors in series to achieve a voltage of 700 to 950 volts.

Electrolytic capacitors are used in ICDs because of their properties in terms of size, reliability and ability to withstand relatively high voltage. Conventionally, such electrolytic capacitors include an etched aluminum foil anode, an aluminum foil or film cathode, and an interposed kraft paper or fabric gauze separator impregnated with a solvent-based liquid electrolyte. While aluminum is typically used for the anode foils, other metals such as tantalum, magnesium, titanium, niobium, zirconium and zinc may be used.

A typical solvent-based liquid electrolyte may be a mixture of a weak acid and a salt of a weak acid, preferably a salt of the weak acid employed, in a polyhydroxy alcohol solvent. The electrolytic or ion-producing component of the electrolyte is the salt that is dissolved in the solvent.

Electrolytic capacitors are typically formed into flat or cylindrical shapes. For a flat construction, the individual cathode and anode foils or plates are stacked in an interleaved manner with separators, such as those disclosed in the above-mentioned U.S. Pat. No. 5,131,388, interposed there between. For a cylindrical construction, the stacked plates are then rolled up into the form of a substantially cylindrical body, or wound roll, that is held together with adhesive tape and is encased, with the aid of suitable insulation, in an aluminum tube or canister. In both the flat and cylindrical constructions, connections to the anode and the cathode are made via tabs.

BRIEF DESCRIPTION OF THE DRAWINGS/FIGURES

The accompanying drawings, which are incorporated herein and form a part of the specification, illustrate embodiments of the present disclosure and, together with the description, further serve to explain the principles of the disclosure and to enable a person skilled in the pertinent art to make and use the embodiments.

FIG. 3A illustrates a D-shaped electrolytic capacitor.

FIG. 3B illustrates a cross-section of the D-shaped electrolytic capacitor of FIG. 3A.

Figure 1A:
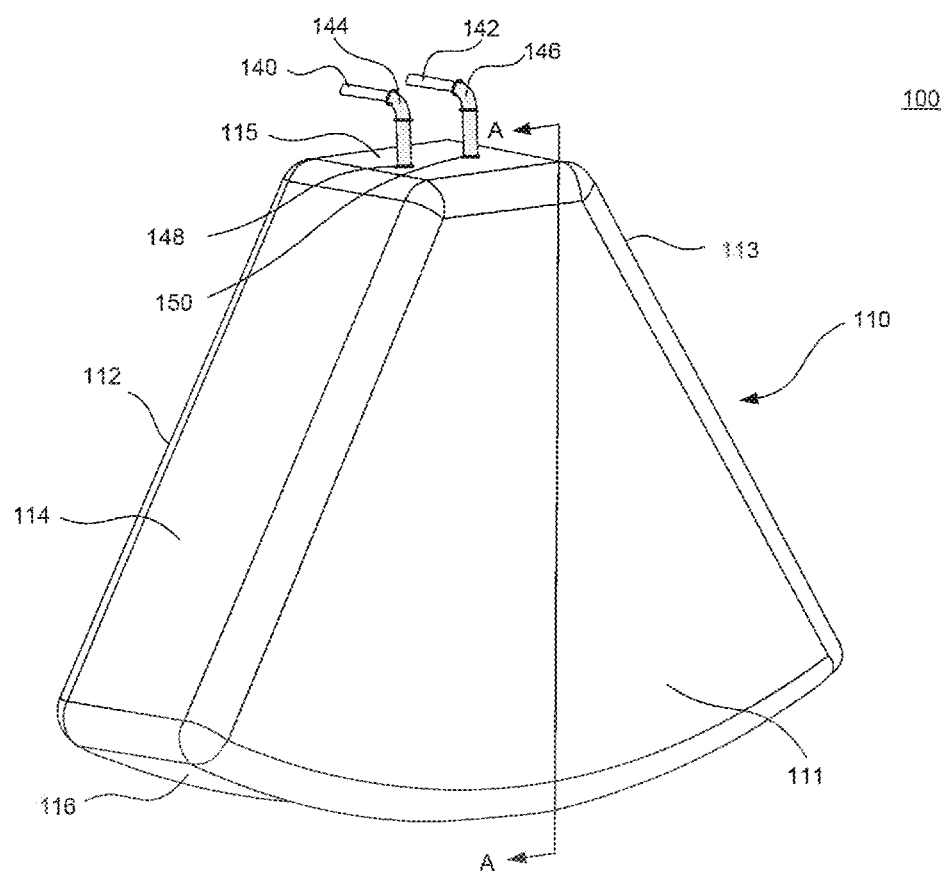
FIG. 1A illustrates an electrolytic capacitor, according to an embodiment of the present disclosure.

The present disclosure will be described with reference to the accompanying drawings. In the drawings, like reference numbers indicate identical or functionally similar elements. Additionally, the left most digit(s) of a reference number identifies the drawing in which the reference number first appears.

DETAILED DESCRIPTION

The following detailed description of apparatuses and methods for processing high voltage capacitors refers to the accompanying drawings that illustrate exemplary embodiments consistent with these apparatuses and methods. Other embodiments are possible, and modifications may be made to the embodiments within the spirit and scope of the apparatuses and methods presented herein. Therefore, the following detailed description is not meant to limit the apparatuses and methods described herein. Rather, the scope of these methods and systems is defined by the appended claims.

It would be apparent to one of skill in the art that the apparatuses and methods for processing high voltage capacitors, as described below, may be implemented in many different embodiments without departing from the scope of the description below. Thus, the operation and behavior of the apparatuses and methods will be described with the understanding that modifications and variations of the embodiments are possible, given the level of detail presented herein. It will be apparent to a person skilled in the relevant art that the apparatuses and methods also be employed to produce high voltage capacitors for use in a variety of devices and applications in addition to use in an implantable cardioverter defibrillator (ICD).

In an ICD, or a subcutaneous ICD (S-ICD), a capacitor assembly is required to store and deliver high voltage energy up to 80 joules at 1350 volts. Traditional designs of high voltage capacitors have been in the shape of a rectangle, square, or semi-circle (D-shape). For these designs, each capacitor in a capacitor assembly typically handles voltage up to 450 volts. Since power is a function of voltage squared ($P=V^2/R$), two or more capacitors are typically connected in series to increase total voltage of the capacitor assembly.

In ICDs, as in other applications where space is a critical design element, it is desirable to use capacitors with the greatest possible capacitance per unit volume. In aluminum electrolytic capacitors, the anode surface A is related to foil capacitance C according to the following equation:

$$C = \in A/d$$

where ∈ is permittivity and d is the thickness between electrodes. Further, the energy of a capacitor is related to foil capacitance by the following equation:

$$E = 0.5CV^2$$

where V is voltage. Since the capacitance of an electrolytic capacitor is provided by the anodes, a clear strategy for increasing the energy density in the capacitor is to minimize the volume taken up by separators and cathodes and maximize the number and the volume of anodes. Additionally, increasing the active anode surface area in a capacitor leads to higher energy per volume at the same working voltage.

The present disclosure recognizes and addresses several shortcomings of conventional capacitors, as will be described later. This disclosure describes an electrolytic capacitor having a housing in an arced-trapezoidal shape. In the present application, an arced-trapezoidal shape is any shape that is formed of four sides having two congruent legs, a short base, and a long base where the long base of the trapezoid is arced between the two congruent legs. Disposed within the housing are one or more anodes, one or more cathodes, one or more separators disposed between anodes that are adjacent anodes cathodes, and an electrolyte disposed around the one or more anodes, the one or more cathodes, and the one or more separators within the housing. The housing of the electrolytic capacitor includes front and back walls shaped as arced-trapezoids and four sidewalls that substantially follow the outline of the front and back walls. The electrolytic capacitor is configured to connect in series with one or more electrolytic capacitors of the same shape to form a capacitor assembly. According to an embodiment, electrolytic capacitors are placed such that sidewalls are adjacent to each other to form a capacitor assembly having a D-shaped arrangement of capacitors that includes an increased total surface area of anodes as compared with traditional capacitor assemblies.

Figure 1B:
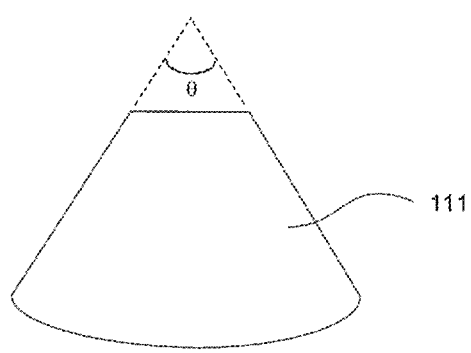
FIG. 1B illustrates another view of the electrolytic capacitor of FIG. 1A, according to an embodiment of the present disclosure.
Figure 1C:
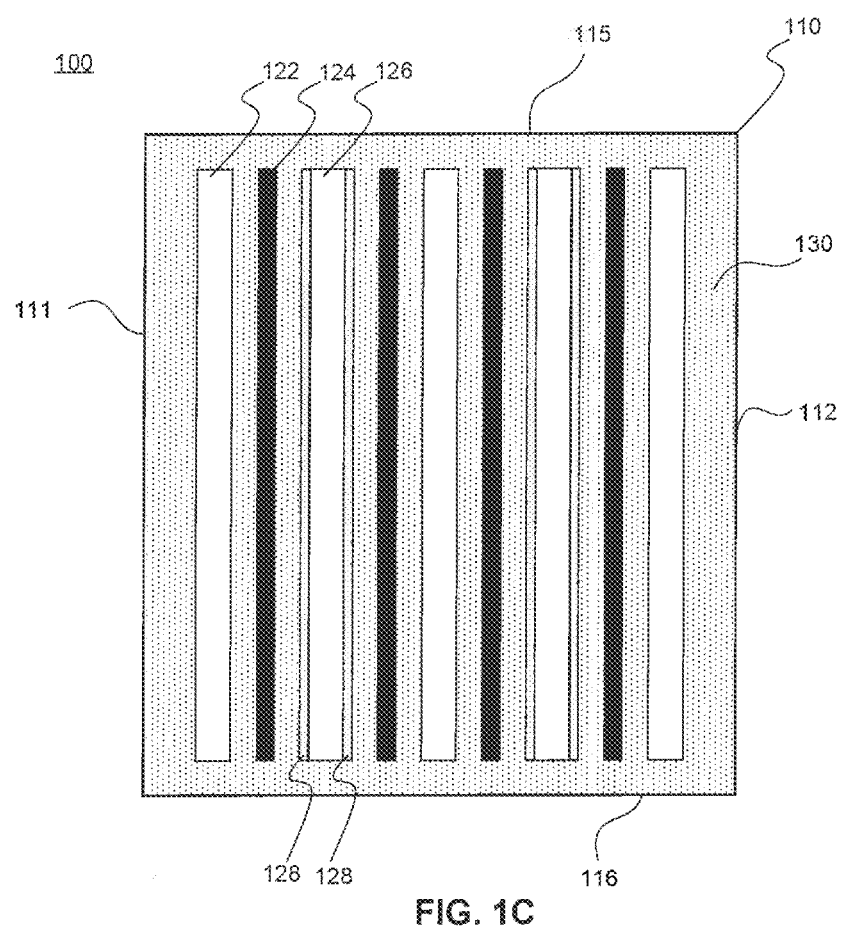
FIG. 1C illustrates a cross-section of the electrolytic capacitor of FIG. 1A, according to an embodiment of the present disclosure.

FIG. 1A illustrates an electrolytic capacitor 100, according to an embodiment of the present disclosure. FIG. 1B illustrates a view of a front wall ill of the electrolytic capacitor of FIG. 1A, according to an embodiment of the present disclosure. FIG. 1C illustrates a cross-section of electrolytic capacitor 100 of FIG. 1A taken along plane A-A, according to an embodiment of the present disclosure. Capacitor 100 includes a housing 110 containing a plurality of cathodes 122 alternating with a plurality of anodes 126, and separated by a plurality of separators 124. Each anode 126 includes a dielectric material 128 on or around an outer surface of anode 126. Dielectric material 128 may be an oxide that is thermally grown on, or deposited onto, the surface of anode 126. A high-k (i.e., a high-dielectric constant) dielectric material may be used for dielectric material 128. A conductive electrolyte 130 fills the space between each of the elements within housing 110. Electrolyte 130 may be a polymer or liquid electrolyte as would be understood by one skilled in the art. Example electrolytes include ethylene glycol/boric acid based electrolytes and anhydrous electrolytes based on organic solvents such as dimethylformamide (DMF), dimethylacetamide (DMA), or gamma-butyrolactone (GBL). Each of the plurality of cathodes 122 includes a tab (not shown), and each of the plurality of anodes 126 includes a tab (not shown). Tabs for the plurality of cathodes 122 are connected together, for example, through a welding process, and electrically connected to a terminal of conductive lead 140. Likewise, tabs for the plurality of anodes 126 are connected together, for example, through a welding process, and electrically connected to a terminal of conductive lead 142.

Example materials used by electrolytic capacitor 100 for the plurality of cathodes 122 include aluminum, titanium, stainless steel, while example materials for the plurality of anodes 126 include aluminum and tantalum. Spacer 124 may be provided to maintain a given separation between each cathode 122 and an adjacent anode 126 within housing 110. Additionally, spacer 124 may be provided to prevent arcing between cathode 122 and anode 126 in spaces where dielectric 128 may be very thin or nonexistent, and/or where a void within electrolyte 130 exists between cathode 122 and anode 126. Spacer 124 may include kraft paper or fabric gauze impregnated with a solvent-based liquid electrolyte.

As shown by FIGS. 1A-1C, housing 110 includes front and rear walls 111, 112, where one or both of front and rear walls 111, 112 may be a lid for accessing cathode 122, spacer 124, anode 126, dielectric 128, and electrolyte 130. Front and rear walls 111, 112 of housing 110 are each shaped as an arced-trapezoid. In this case, front and rear walls 111, 112 include two congruent straight sides that oppose each other, a third straight side that forms the shortest segment of the four sides, and an arced side opposite the third straight side, as shown by FIG. 1A. As shown by FIG. 1B the congruent sides of the arced-trapezoid shape are separated by angle θ. Housing 110 also includes four sidewalls, straight sidewalls 113, 114, 115 and arced sidewall 116, that substantially follow the outline of the front and rear walls 111, 112. Straight sidewalls 113, 114, 115 and arced sidewall 116 contact the sides of front and rear walls 111, 112. Straight sidewalls 113, 114, 115 are also positioned between front and rear walls 111, 112 to maintain a given separation such that front and rear walls 111, 112 are substantially parallel to each other. Straight sidewalls 113, 114 are congruent to each other and are positioned between straight sidewall 115 and arced sidewall 116, which oppose each other. Front and rear walls 111, 112 of housing 110 are not limited to an arced-trapezoid shape and may be in other shapes, as described in further detail below.

An exemplary material used for manufacturing the housing 110 may be formed of aluminum. Conductive leads 140, 142 extend from an interior of housing 110 through apertures 148, 150 in straight wall 115 for connection to other circuitry. Conductive leads 140, 142 may be wrapped in insulative sleeves 144, 146 such that no electrical contact is made between conductive leads 140, 142 and housing 110. Further, insulative sleeves 144, 146 may help in creating an environmental seal for housing 110.

It should be understood that the various elements and dimensions of electrolytic capacitor 100 are not drawn to scale. Although each of the plurality of cathodes 122, the plurality of separators 124, and the plurality of anodes 126 are illustrated as being spaced apart from one another for the convenience of illustration and labeling, it would be understood by one skilled in the art that such elements may also be stacked together in close physical contact with one another.

Figure 2:
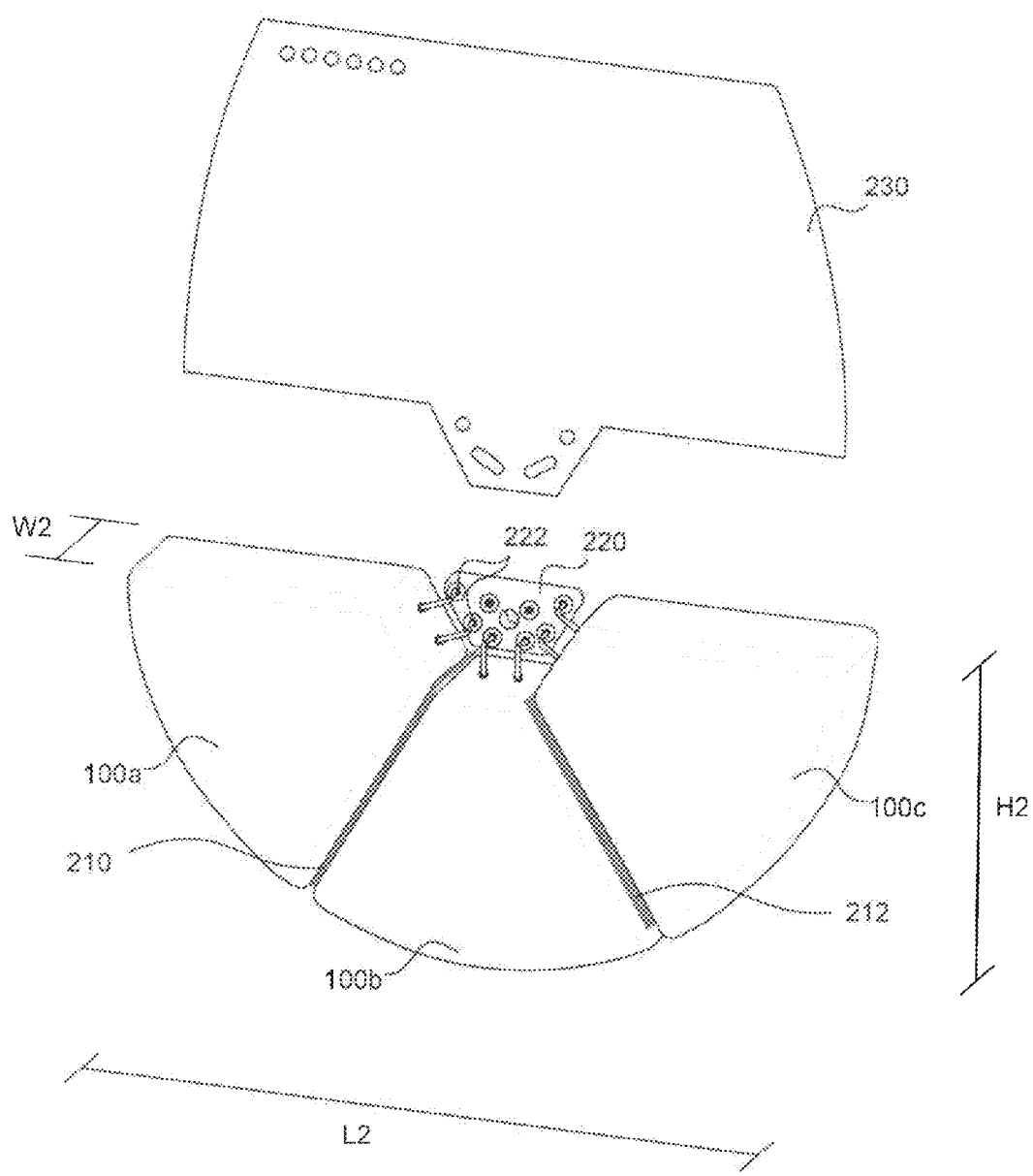
FIG. 2 illustrates a capacitor assembly, according to an embodiment of the present disclosure.

FIG. 2 illustrates capacitor assembly 200, according to exemplary embodiments of the present disclosure. Capacitor assembly 200 includes three electrolytic capacitors 100a, 100b, 100c arranged in a semi-circular shape, as shown by FIG. 2. Electrolytic capacitors 100a, 100b, 100c are exemplary embodiments of capacitor 100 and naming conventions 100a, 100b, 100c are used for convenience in describing relative locations within capacitor assembly 200. In capacitor assembly 200, angle θ is 60° such that the three capacitors 100a, 100b, 100c are positioned to form the semi-circular shape. However, embodiments of the present disclosure are not limited to an angle of 60°. For example, in an embodiments, angle θ may be 90°, such that only two capacitors are required to form the semi-circular shape, and in yet another embodiment, angle θ may be 45°, such that four capacitors are used to form the semi-circular shape.

Capacitor assembly 200 further includes insulator 210 which is disposed between adjacent sidewalls of capacitor 100a, 100b, and insulator 212 which is disposed between adjacent sidewalls of capacitors 100b, 100c. Exemplary materials used for manufacturing insulators 210, 212 include a polymer such as polyimide.

As shown by FIG. 2, each of the capacitors 100a, 100b, 100c are connected in series through connection assembly 220 such as a spring receptacle assembly or socket assembly. For connection, conductive leads 140, 142 for each of the capacitors 100a, 100b, 100c are inserted into apertures 222 of connection assembly 220 by way of contact to springs or solder, to provide an example. Connection assembly 220 may then be attached to printed circuit board (PCB) 230 for use in an electronic device, such as an ICD.

The following description is provided to illustrate differences between the present disclosure and conventional art. FIG. 3A illustrates a D-shaped electrolytic capacitor. FIG. 3B illustrates a cross-section of the D-shaped electrolytic capacitor of FIG. 3A. As shown by FIGS. 3A-3B, capacitor assembly 300 includes three capacitors 310, 320, 330. Electrolytic capacitors 310, 320, 330 are individually manufactured and then stacked on top of each other. When stacked, electrolytic capacitors 310, 320, 330 are separated by insulators. As shown by FIG. 3B, insulator 340 is disposed between case walls 312, 322 of capacitors 310, 320, and insulator 350 is disposed between case walls 324, 332 of capacitors 320, 330. As shown by FIGS. 3A-3B, case walls 312, 322, 324, 332 include the largest surface areas of capacitors 310, 320, 330. By depositing insulators 340, 350 on these surfaces for assembly purposes, a substantial amount of surface area and volume is consumed not only by insulators 340, 350 but also by case walls 312, 322, 324, 332.

Assuming that width W2, length L2, and height H2 of capacitor assembly 200 of FIGS. 2A-2B are substantially the same as width W3, length L3, and height H3, respectively, of capacitor assembly 300 of FIG. 3, an anode surface area of the capacitor assembly 200 is 36% more than a anode surface area of the capacitor assembly 300. This is due to a substantial decrease in an amount of surface area and volume of the insulators and case walls used between adjacent capacitors 100a, 100b, 100c. This can be understood by the following real world example where, aside from the shape of individual capacitors, the footprint size and volume of capacitor assembly 200 and capacitor assembly 300 are substantially the same such that a capacitor assembly (e.g., capacitor assembly 200) having three capacitors in series includes a total of 70 anode foils with a total anode surface area of 115.998 in², and a capacitor assembly (e.g., capacitor assembly 300) having three capacitors in series includes a total of 18 anode foils with a total surface area of 84.894 in².

Due to the increase in total surface area of the anode, an energy density of the aluminum electrolytic capacitor assembly 200 can reach higher than 5.5 J/cc which leads to a significant decrease in the overall volume of the capacitor assembly. In other words, the capacitor assembly 200 can have a 36% reduction in size, as compared to the capacitor assembly 300, and still retain the same amount of energy density.

Figure 4:
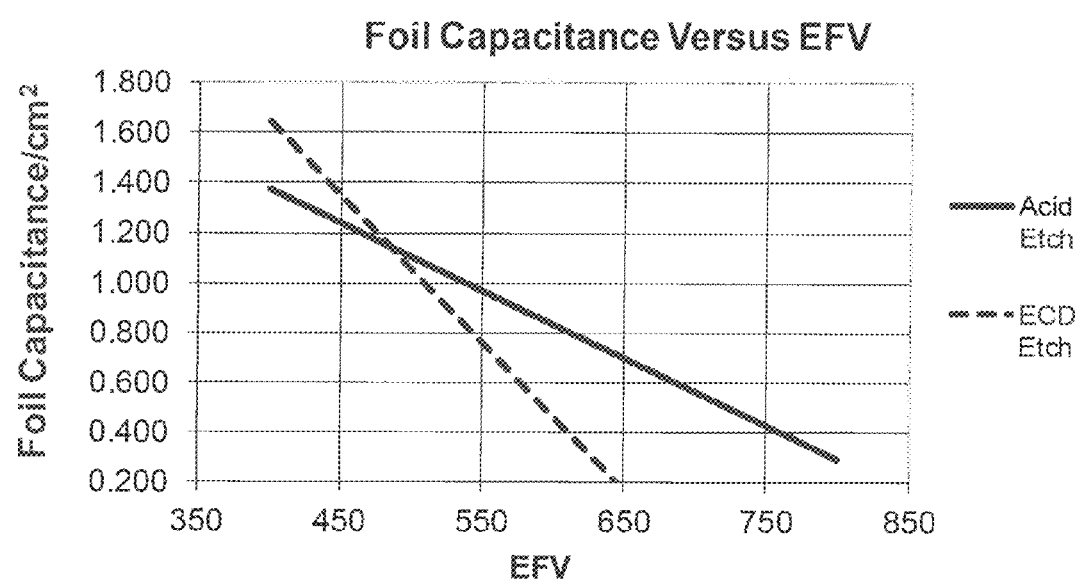
FIG. 4 illustrates foil capacitance versus the effective formation voltage (EFV) according to embodiments of the present disclosure.
Figure 5:
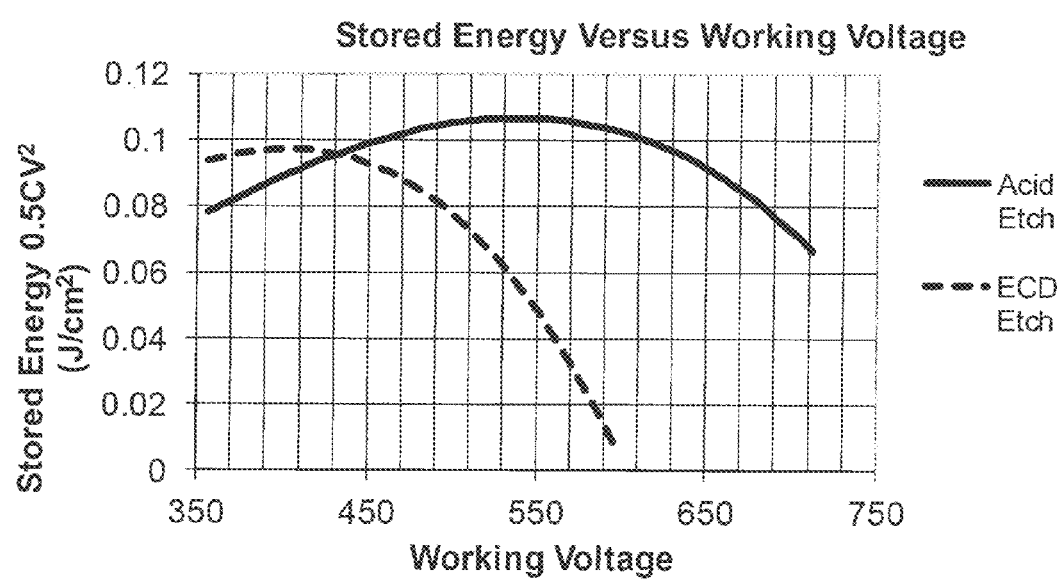
FIG. 5 illustrates stored energy versus working voltage, according to embodiments of the present disclosure.

Advantages of the embodiments of the present disclosure are further illustrated with FIGS. 4-5. In particular, FIG. 4 illustrates foil capacitance versus the effective formation voltage (EFV) according to embodiments of the present disclosure. FIG. 5 illustrates stored energy versus working voltage, according to embodiments of the present disclosure. As shown by FIG. 4, as a capacitor increases to a higher EFV, capacitance decreases. This is both true for an acid etch process and a neutral etch process (e.g., an electrochemical drilling (ECD) process.) However, as shown by FIG. 4, capacitance decreases at a slower pace for the acid etch process as compared to the ECD process. As shown by FIG. 5, the stored energy (i.e., $E=0.5CV^2$) is greater for an acid etche process as the capacitance decreases such that an optimum voltage of the acid etch process is at a higher voltage (e.g., 550 working volts) than the optimum voltage for the ECD process (e.g., 410 working volts). Thus, the capacitor assembly 200 allows for each capacitor to run at a typical working voltage (e.g., 450 volts having a total voltage of 1350) with an optimized energy density that is greater than typical capacitor assemblies.

Further, due to the formation of the capacitor assembly 200, a formation derating factor (i.e., EFV per working voltage) is maintained such that low leakage current and low deformation occur in the capacitor assembly which leads to a longer life for an ICD or S-ICD.

Figure 6:
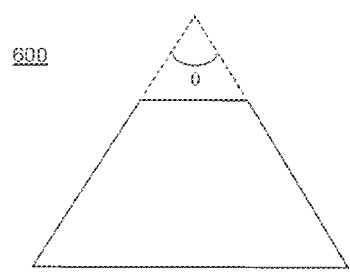
FIGS. 6-8 illustrate top-down views of housing shapes for electrolytic capacitors, according to embodiments of the present disclosure.
Figure 7:
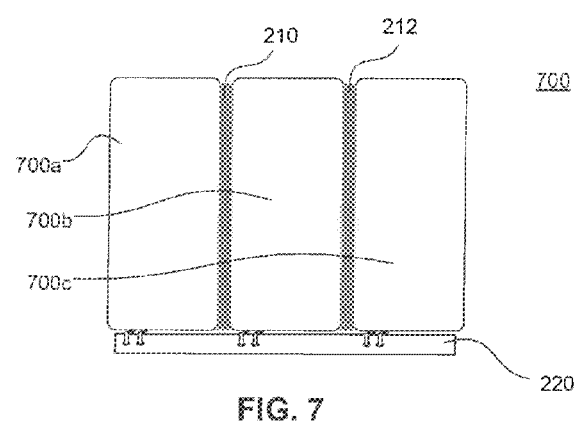
Figure 8:
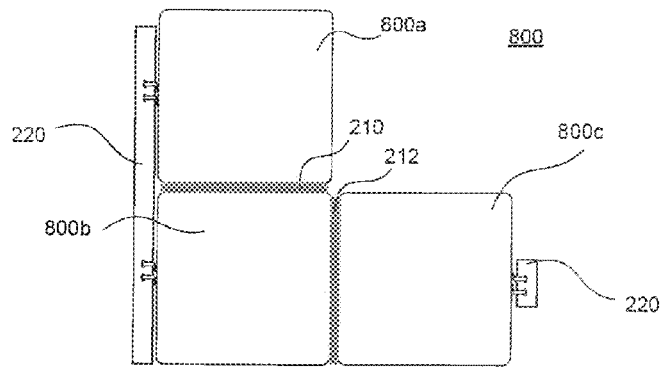

FIGS. 6-8 illustrate top-down views of housing shapes for electrolytic capacitors, according to embodiments of the present disclosure. As described above, housing 110 is not limited to an arced-shaped trapezoid. Instead, embodiments of the present disclosure may include capacitors having front and rear walls shaped in the form of a trapezoid, as illustrated by FIG. 6. According to an embodiment, a base of capacitor 600 is straight instead of arced liked capacitor 100, as shown by FIG. 1B. In a capacitor assembly, adjacent sidewalls of capacitor 600 having a trapezoid shaped housing, as shown in FIG. 6, are positioned similar to those as described with capacitor assembly 200. As shown by FIG. 7, capacitors 700a, 700b, 700c include front and rear walls shaped in the form of a rectangle, and as shown by FIG. 8, capacitors 800a, 800b, 800c include front and rear walls shaped in the form of a square. Similar to capacitor assembly 200, capacitors in capacitor assemblies 700 and 800 are arranged such that adjacent sidewalls, and not front and rear walls, of the capacitors are separated by insulators 210, 212 resulting in an increased total anode surface area, as compared to the traditional capacitor assemblies, such as capacitor assembly 300.

CONCLUSION

It is to be appreciated that the Detailed Description section, and not the Summary and Abstract sections, is intended to be used to interpret the claims. The Summary and Abstract sections may set forth one or more but not all exemplary embodiments of the present apparatuses and methods as contemplated by the inventors, and thus, are not intended to limit the present apparatuses and methods and the appended claims in any way.

Moreover, while various embodiments of the present apparatuses and methods have been described above, it should be understood that they have been presented by way of example, and not limitation. It will be apparent to persons skilled in the relevant art(s) that various changes in form and detail can be made therein without departing from the spirit and scope of the present apparatuses and methods. Thus, the present apparatuses and methods should not be limited by any of the above described exemplary embodiments, but should be defined only in accordance with the following claims and their equivalents.

In addition, it should be understood that the figures, which highlight the functionality and advantages of the present apparatuses and methods, are presented for example purposes only. Moreover, the steps indicated in the exemplary apparatuses and methods described above may in some cases be performed in a different order than the order described, and some steps may be added, modified, or removed, without departing from the spirit and scope of the present system and method.

What is claimed is:

1. A capacitor assembly, comprising:
 a plurality of capacitors each having:
  a housing having an arced-trapezoidal shape;
  one or more anodes disposed within the housing;
  one or more cathodes disposed within the housing;
  one or more separators disposed between an anode of the one or more anodes adjacent to a cathode of the one or more cathodes; and
  an electrolyte disposed around the one or more anodes, the one or more cathodes, and the one or more separators within the housing.

2. The capacitor assembly of claim 1, wherein insulation is disposed between adjacent external sidewalls of the plurality of capacitors.

3. The capacitor assembly of claim 2, wherein the plurality of capacitors include three capacitors.

4. The capacitor assembly of claim 3, wherein the plurality of capacitors are positioned adjacent to each other to form a semi-circle.

5. The capacitor assembly of claim 4, wherein each of the plurality of capacitors includes conductive leads that are connected in series.

6. The capacitor assembly of claim 5, wherein the conductive leads for each of the plurality of capacitors include a first conductive lead connected to the one or more anodes and a second conductive lead connected to the one or more cathodes.

7. The capacitor assembly of claim 5, further comprising a connection assembly, wherein the conductive leads are attached in series by way of the connection assembly.

8. The capacitor assembly of claim 7, wherein the connection assembly is a spring receptacle assembly.

9. The capacitor assembly of claim 7, further comprising a printed circuit board, wherein the printed circuit board connects to the connection assembly.

10. An electrolytic capacitor, comprising:
 one or more anodes;
 one or more cathodes;
 one or more separators disposed between the one or more anodes adjacent to the one or more cathodes;
 an electrolyte disposed around the one or more anodes, the one or more cathodes, and the one or more separators; and
 a housing formed in an arced-trapezoidal shape, wherein the one or more anodes, the one or more cathodes, the one or more separators, and the electrolyte are disposed within the housing.

11. The electrolytic capacitor of claim 10, wherein the housing includes a front wall and a rear wall shaped as an arced trapezoid, wherein at least one of the front wall and the rear wall is a lid to the housing.

12. The electrolytic capacitor of claim 11, wherein the housing further includes:
 a first straight sidewall;
 a second straight sidewall congruent to the first straight sidewall;
 a third straight sidewall contacting a first edge of the first straight sidewall and a first edge of the second straight sidewall; and
 an arced sidewall opposed to the third straight wall and contacting a second edge of the first straight sidewall and a second edge of the second straight sidewall.

13. The electrolytic capacitor of claim 10, further comprising:
 a first conductive lead connected to the one or more anodes; and
 a second conductive lead connected to the one or more cathodes.

14. The electrolytic capacitor of claim 13, wherein the third straight sidewall includes first and second apertures for the first conductive lead and the second conductive lead, respectively, such that the first conductive lead and the second conductive lead extend from an inside of the housing to an exterior of the housing by way of the first and second apertures.

15. The electrolytic capacitor of claim 10, wherein the one or more anodes, the one or more cathodes, and the one or more separators are arranged in a stacked formation.

16. The electrolytic capacitor of claim 10, wherein the housing is formed of aluminum.

17. A capacitor assembly, comprising:
 a first electrolytic capacitor including:
  a housing having front and rear walls having a geometric shape and at least one sidewall; and
 a second electrolytic capacitor including:
  a housing having front and rear walls having the geometric shape and at least one sidewall,
 wherein the at least one sidewall of the first electrolytic capacitor and the one sidewall of the second electrolytic capacitor are arranged adjacent to each other.

18. The capacitor assembly of claim 17, further comprising insulators, wherein the insulators are disposed between the adjacent sidewalls of the first and second electrolytic capacitors.

19. The capacitor assembly of claim 17, wherein the housing for the first electrolytic capacitor and the housing for the second electrolytic capacitor is formed of aluminum.

20. The capacitor assembly of claim 17, wherein at least one of the front and rear walls of the first electrolytic capacitor is a first lid, and at least one of the front and rear walls of the first electrolytic capacitor is a second lid.

* * * * *